US012564627B2

(12) United States Patent
Pisharodi

(10) Patent No.:　US 12,564,627 B2
(45) Date of Patent:　　Mar. 3, 2026

(54) SYSTEM FOR PRODUCING AND DELIVERING CONTACTLESS VETERINARY PASSIVE IMMUNIZATION

(71) Applicant: Madhavan Pisharodi, Brownsville, TX (US)

(72) Inventor: Madhavan Pisharodi, Brownsville, TX (US)

(73) Assignee: PERUMALA HOLDINGS, LLC, Brownsville, TX (US)

( * ) Notice: Subject to any disclaimer, the term of this patent is extended or adjusted under 35 U.S.C. 154(b) by 0 days.

(21) Appl. No.: 19/203,759

(22) Filed: May 9, 2025

(65) Prior Publication Data

US 2025/0262295 A1　　Aug. 21, 2025

Related U.S. Application Data

(63) Continuation-in-part of application No. 18/407,208, filed on Jan. 8, 2024, now Pat. No. 12,298,037, which is a continuation-in-part of application No. 18/328,463, filed on Jun. 2, 2023, now Pat. No. 12,194,206, and a continuation-in-part of application No. 18/058,185, filed on Nov. 22, 2022, now Pat. No. 11,951,164, which is a continuation-in-part of application No. 17/545,822, filed on Dec. 8, 2021, now Pat. No. 11,511,013, said application No. 18/328,463 is a continuation-in-part of application No. 18/058,185, filed on Nov. 22, 2022, now Pat. No. 11,951,164.

(60) Provisional application No. 63/479,143, filed on Jan. 9, 2023, provisional application No. 63/401,817, filed on Aug. 29, 2022, provisional application No. 63/359,381, filed on Jul. 8, 2022, provisional application No. 63/353,369, filed on Jun. 17, 2022, provisional application No. 63/233,697, filed on Aug. 16, 2021.

(51) Int. Cl.
　　*A61K 39/215*　　(2006.01)
　　*A61M 16/10*　　(2006.01)
　　*C12N 7/00*　　(2006.01)
　　*A61K 39/00*　　(2006.01)

(52) U.S. Cl.
　　CPC ........... *A61K 39/215* (2013.01); *A61M 16/10* (2013.01); *C12N 7/00* (2013.01); *A61K 2039/5252* (2013.01); *A61M 2202/20* (2013.01); *C12N 2770/20034* (2013.01); *C12N 2770/20061* (2013.01)

(58) Field of Classification Search
None
See application file for complete search history.

(56) References Cited

U.S. PATENT DOCUMENTS

| 3,721,072 | A | | 3/1973 | Miller |
| 3,773,044 | A | | 11/1973 | Wallace |
| 3,850,170 | A | | 11/1974 | Cox |
| 4,580,556 | A | | 4/1986 | Kondur |
| 4,742,760 | A | | 5/1988 | Horstman |
| 5,656,242 | A | | 8/1997 | Morrow et al. |
| 7,185,510 | B2 | | 3/2007 | Lee et al. |
| 8,336,821 | B2 | | 12/2012 | Shell et al. |
| 8,674,322 | B2 | | 3/2014 | Kohler |
| 11,052,169 | B1 | | 7/2021 | Pisharodi |
| 12,298,037 | B2 | * | 5/2025 | Pisharodi .................. F24F 8/22 |
| 2006/0057020 | A1 | | 3/2006 | Tufo |
| 2006/0263276 | A1 | | 11/2006 | Pattee |
| 2008/0112845 | A1 | | 5/2008 | Dunn |
| 2008/0173178 | A1 | | 7/2008 | Metteer |
| 2010/0150793 | A1 | | 6/2010 | Chan |
| 2011/0286167 | A1 | | 11/2011 | Winkler |
| 2012/0128539 | A1 | | 5/2012 | Gross et al. |
| 2012/0301363 | A1 | | 11/2012 | Kim et al. |
| 2016/0001108 | A1 | | 1/2016 | Zhou et al. |
| 2017/0341762 | A1 | | 11/2017 | Breigenzer |
| 2018/0250430 | A1 | | 9/2018 | Machovina et al. |
| 2019/0009912 | A1 | | 1/2019 | Matsui |
| 2020/0155667 | A1 | | 5/2020 | James et al. |

FOREIGN PATENT DOCUMENTS

WO　WO-2022090586 A1 *　5/2022

OTHER PUBLICATIONS

'How a packaged system works' (Goodman) Jul. 29, 2016, [online] retrieved from <URL: https://web.archive.org/web/20160729193422/ https://www.goodmanmfg.com/resources/heating-cooling-101/how-a-packaged-system-works>.
Hankaniemi et al., Vaccine, vol. 37, Issue 40, pp. 5962-5971, (Year: 2019).
'UVC disinfects SARS CoV 2 by induction of viral genome damage without apparent effects on viral morphology and proteins' (Lo) Jul. 5, 2021, [online] retrieved from <URL: https://doi.org/10.1038/ s41598-021-93231-7>.
'UV Inactivation of Rotavirus and Tulane Virus Targets Different Components of the Virions' (Araud) Feb. 3, 2020, [online] retrieved from <URL: https://doi.org/10.1128/AEM.02436-19.>.
W. C. Russell; "Adenoviruses: update on structure and function;" Journal of General Virology (2009), 90, 1-20; DOI 10.1099/vir.0. 003087-0.
'Ultraviolet A light effectively reduces bacteria and viruses including coronavirus' (Rezale) Jul. 16, 2020, [online] retrieved from <URL: https://doi.org/10.1371/journal.pone.0236199>.

(Continued)

*Primary Examiner* — Shanon A. Foley
*Assistant Examiner* — Myron G Hill
(74) *Attorney, Agent, or Firm* — D'Ambrosio & Menon, PLLC; Usha Menon

(57) ABSTRACT

A system and method for passively delivering inactivated pathogens to a population of animals or birds. The method comprises: isolating a pathogen from an infected animal/ bird; culturing the isolated pathogen; inactivating the isolated pathogen with UVC; infusing an object with the inactivated pathogen; and introducing the inactivated pathogen infused object into an area containing one or more animals/birds.

5 Claims, 10 Drawing Sheets

(56)         References Cited

OTHER PUBLICATIONS

Koma T, Doi N, Suzuki A, Nagamatsu K, Yasui T, Yasutomo K, Adachi A, Minamikawa T and Nomaguchi M (2022) Major target for UV-induced complete loss of HIV-1 infectivity: A model study of single stranded RNA enveloped viruses. Front. Virol. 2:994842. doi: 10.3389/fviro.2022.994842.

'UV C irradiation is highly efective in inactivating SARS CoV 2 replication' (Biasin) Mar. 18, 2021, [online] retrieved from <URL: https://doi.org/10.1038/s41598-021-85425-w>.

Eischeid, Anne C. et al; "Molecular Indications of Protein Damage in Adenoviruses after UV Disinfection;" Applied and Environmental Microbiology, Feb. 2011, p. 1145-1147 vol. 77, No. 3.

Araud E, Fuzawa M, Shisler JL, Li J, Nguyen TH. 2020. UV inactivation of rotavirus and Tulane virus targets different components of the virions. Appl Environ Microbiol 86:e02436-19. https://doi.org/10.1128/AEM 02436-19.

Ma B, Gundy PM, Gerba CP, Sobsey MD, Linden KG. 2021. UV inactivation of SARSCoV-2 across the UVC spectrum: KrCI* excimer, mercury-vapor, and light-emitting-diode (LED) sources. Appl Environ Microbiol 87: e01532-21. https://doi.org/10.1128/AEM.01532-21.

Christin Scheller; "Physicochemical properties of SARS-CoV-2 for drug targeting, virus inactivation and attenuation, vaccine formulation and quality control" Electrophoresis 2020, 41, pp. 1137-1151; Wiley-VCH Verlag Gmbh & Co. KGaA.

George Devitt et al; "Mechanisms of SARS-CoV-2 Inactivation using UVC Laser Radiation" bioRxiv preprint Feb. 3, 2023.; https://doi.org/10.1101/2023.02.03.526944doi.

Ernest R. Blatchley, III et al; "SARS-CoV-2 Ultraviolet Radiation Dose-Response Behavior" SARS-CoV-2 Ultraviolet Radiation Dose-Response Behavior; Journal of Research of the National Institute of Standards and Technology; vol. 126, Article No. 126018 (2021) https://doi.org/10.6028/jres.126.018.

Ernest R. Blatchley, III et al; "Far UV-C Radiation: Current State-of Knowledge" International Ultraviolet Association; Whitepaper of The IUVA Task Force (TF) on Far UV-C Radiation for Disinfection of Air and Surfaces; May 14, 2021. https://iuva.org/Projects-Articles-Repository/10503221.

Beck, Sara E. et al. "Wave-length dependent Damage to Adenoviral Proteins Across the Germacidal UV Spectrum" Environ. Sci. Technol. 2018, 52, 223-229.

Joshua Hadi et al; "Control Measures for SARS-CoV-2: A Review on Light-Based Inactivation of Single-Stranded RNA Viruses" Pathogens 2020, 9, 737; doi:10.3390/pathogens9090737; http://www.mdpi.com/journal/pathogens.

Sanjeev K. Bhardwaj et al "UVC-based photoinactivation as an efficient tool to control the transmission of coronaviruses" Science of the Total Environment 792 (2021) 148548; www.elsevier.com/locate/scitotenv.

Loveday, E.K.; Hain, K.S.; Kochetkova, I.; Hedges, J.F.; Robison, A.; Snyder, D.T.; Brumfield, S.K.; Young, M.J.; Jutila, M.A.; Chang, C.B.; et al. Effect of Inactivation Methods on SARS-CoV-2 Virion Protein and Structure. Viruses 2021, 13, 562. https://doi.org/10.3390/v13040562.

Naomi Takasuka et al; "A subcutaneously injected UV-inactivated SARS coronavirus vaccine elicits systemic humoral immunity in mice" International Immunology, vol. 16, No. 10, pp. 1423-1430; 2004; The Japanese Society for Immunology; doi:10.1093/intimm/dxh143.

Ong, Q. et al; "Irradiation of UVC LED 277 nm inactives coronaviruses in association to photodegradation of spike protein;" Helion 8 (2022) e11132; www.cell.com/heliyon.

Renata Sesti-Costa et al; "UV 254 nm is more efficient than UV 222 nm in inactivating SARS-CoV-2 present in human saliva;" Photodiagnosis and Photodynamic Therapy 39 (2022) 103015; https://doi.org/10.1016/j.pdpdt.2022.103015.

* cited by examiner

215

302

208

SYSTEM FOR PRODUCING AND DELIVERING CONTACTLESS VETERINARY PASSIVE IMMUNIZATION

CROSS REFERENCE TO RELATED APPLICATIONS

This application claims priority to and is a continuation-in-part of U.S. Ser. No. 18/407,208 filed on Jan. 8, 2024, which is a non-provisional application of and claims priority to U.S. Provisional Patent Application Ser. No. 63/479,143 filed on Jan. 9, 2023, and also claims priority to and is a continuation in part of U.S. Ser. Nos. 18/328,463 filed on Jun. 2, 2023, which is a continuation-in-part of U.S. Ser. No. 18/058,185 filed on Nov. 22, 2022, and claims priority to U.S. Provisional Patent Application Ser. No. 63/353,369 filed on Jun. 17, 2022, U.S. Provisional Patent Application Ser. No. 63/359,381 filed on Jul. 8, 2022, and U.S. Provisional Patent Application Ser. No. 63/401,817 filed on Aug. 29, 2022. U.S. Ser. No. 18/407,208 also claims priority to and is a continuation of U.S. Ser. No. 18/058,185 filed on Nov. 22, 2022, which claims priority to and is a continuation in part of U.S. Ser. No. 17/545,822 filed on Dec. 8, 2021, which claims priority to and is a non-provisional application of U.S. Ser. No.: 63/233,697 filed on Aug. 16, 2021. The entire disclosures of these patent applications are part of the disclosure of the present application and are hereby incorporated by reference in their entireties.

FIELD OF THE INVENTION

The present invention relates to a novel method for infection control in the environment. In particular, the present invention discloses the inactivation of pathogens using ultraviolet light and a novel delivery system of those inactivated pathogens for inducing a passive immunity in animals.

BACKGROUND

The background description includes information that may be useful in understanding the present invention. It is not an admission that any of the information provided herein is prior art or relevant to the presently claimed invention, or that any publication specifically or implicitly referenced is prior art.

The history of vaccine development has had its ups and downs. The smallpox vaccine, rabies vaccine, and many others were developed even before the causative agents were identified or isolated. Many research professionals sacrificed their lives in the process, most notably the ones in the yellow fever vaccine development. Vaccine development started with live pathogens, mostly attenuated versions of the disease-causing agents. The next phase of vaccine development was by using killed pathogens and the toxoid vaccines. The latest newcomer in the field is the various forms of fragment vaccines, most notably the mRNA vaccines.

The conventional wisdom for vaccine development is that the more similar a vaccine is to the pathogenic virus (agent), the better the immunological response. It is a known fact that most of the human pathogens are transmitted to humans from the original sources from birds, bats, primates, etc. Therefore, there is an ongoing need to provide better infection control systems to treat and protect animals from the spread of infectious diseases.

Aerosol vaccinations were used in the past with limited success in humans, chickens, fowls, pigs etc. Chicken aerosol vaccination was tried against Newcastle disease. Such aerosol vaccines have been tried against anthrax, plague and smallpox. Aerosol vaccines can be produced and dispersed through an aerosol generator and provided to an individual or to a group through a tent or similar structures. Such vaccination is claimed to give local mucosal immunity and generalized systemic immunity. See Roth et al (2003) and Garg et al (2017)

Aerosol vaccines have multiple variability making it somewhat unpredictable. The CDC advised against nasal spray of flu vaccine in 2016 because it was found to have only 3% protective benefit. The conventional aerosol vaccines used jet nebulizers and pressurized air systems and these create stability concerns. As a result, the systems described in Roth and Garg are not clinically reliable.

Therefore, there is a need for systems and methods to overcome these deficiencies and to preferably provide contactless immunization to animal and bird species.

SUMMARY

According to an embodiment, a method for providing contactless immunization for animals or birds involves: isolating a pathogen from an infected animal/bird; culturing the isolated pathogen; inactivating the isolated pathogen with UVC; infusing an object with the inactivated pathogen; and introducing the inactivated pathogen infused object into an area containing one or more animals/birds. The inactivation of the cultivated pathogen is performed using a UVC disinfection unit. The object is selected from the group consisting of floor coverings, nesting materials, and food sources.

One embodiment of the invention is a system for delivering inactivated pathogens to an enclosure comprising an air delivery system. The air delivery system includes: (a) an air intake; (b) an air conditioning unit; (c) an air mover; (d) a UVC disinfection unit; (e) an enclosure configured for holding birds and or animals; (f) an enclosure air entry vent; (g) an enclosure air discharge vent; and (h) an air circulation pathway going from the air intake through an air duct connected at one end to the air intake and at a second end to the enclosure air entry vent that opens into the enclosure, where the air duct provides a passageway through the air delivery system. The air mover can control the velocity of air movement through the air duct.

In one or more embodiments, the UVC disinfection unit comprises a housing that encloses a disinfection chamber that has: (a) a chamber wall; (b) a chamber inlet; (c) a chamber outlet; (d) a centralized inner bore having an interior chamber surface facing the inner bore; (e) a UVC light source positioned adjacent the interior chamber surface; and (f) a helical air flow diverter centralized within the inner bore proximal the UVC light source, wherein the helical airflow diverter creates a helical path for the air circulation pathway to proceed through the disinfection chamber from the chamber inlet to the chamber outlet.

The air disinfection unit can contain more than one UVC disinfection chamber.

The enclosure can be configured as a free-standing and/or mobile/transportable enclosure.

The system can have a pathogen loading inlet connected to the air circulation pathway. In another embodiment, the system can have a test chamber connected to the air circulation pathway adjacent to the UVC disinfection unit. In one or more embodiments, the system is configured as a contactless system for immunizing birds or animals.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

The invention will be described in further detail below and with reference to the attached drawings, which describe or relate to methods and devices of the present invention.

DETAILED DESCRIPTION

Figure 1:
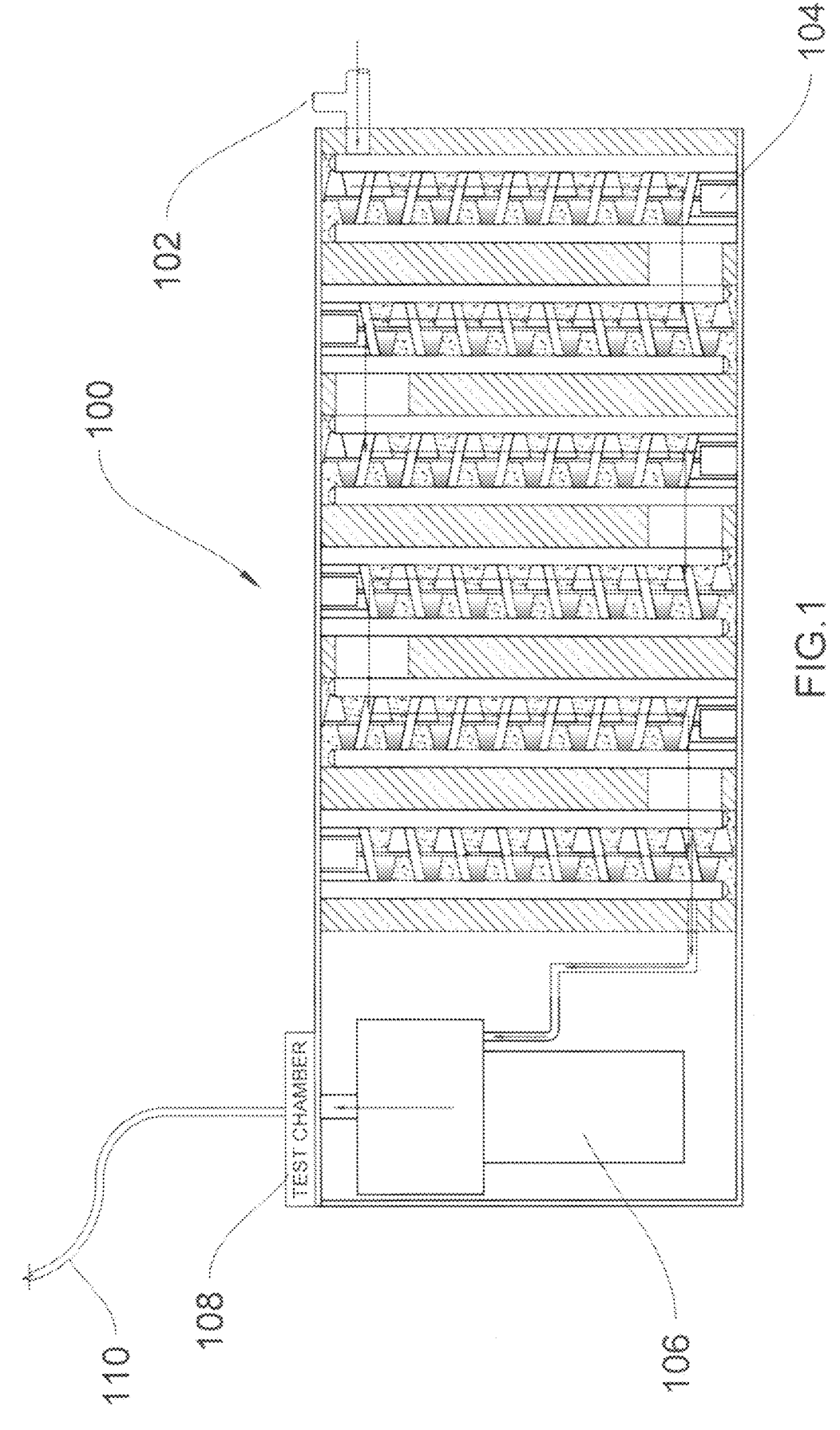
FIG. 1 illustrates an embodiment of a UVC disinfection unit.

Characteristics and advantages of the present disclosure and additional features and benefits will be readily apparent to those skilled in the art upon consideration of the following detailed description of exemplary embodiments. The intention is to cover all modifications, equivalents and alternatives falling within the spirit and scope of this disclosure. Many changes may be made to the particular embodiments and details disclosed herein without departing from such spirit and scope. For instance, although the SARS-COV-2 virus or the H5 virus may be used as an example of the invention, it is understood that the methods and devices disclosed herein can be used for other pathogens, both viruses and bacteria.

As used herein and throughout various portions (and headings) of this patent (including the claims), the terms "invention", "present invention" and variations thereof are not intended to mean every possible embodiment encompassed by this disclosure or any particular claim(s). Thus, the subject matter of each such reference should not be considered as necessary for, or part of, every embodiment hereof, or of any particular claim(s), merely because of such reference. Each of the appended claims defines a separate invention, which for infringement purposes is recognized as including equivalents to the various elements or limitations specified in the claims. Depending on the context, all references below to the "invention" may in some cases refer to certain specific embodiments only. In other cases, it will be recognized that references to the "invention" will refer to subject matter recited in one or more, but not necessarily all, of the claims. As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

All methods described herein can be performed in any suitable order unless otherwise indicated herein or otherwise clearly contradicted by context. The use of any and all examples, or exemplary language (for instance, "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Various terms are used herein. To the extent a term used in a claim is not defined, it should be given the broadest definition persons in the pertinent art have given that term as reflected in printed publications and issued patents at the time of filing.

A present concern in the United States and other countries is the spread of viruses and/or bacteria in domesticated animals, and in the spread of disease across species. For example, the spread of the H5 bird flu from birds in the wild to domesticated birds and then to other species is a major concern. According to the Center for Disease Control there have been numerous poultry and dairy herds affected by bird flu outbreaks within the United States in the last year. In domesticated animals (such as poultry, cattle, and pigs) the bird flu is most commonly spread by infected droppings, food, nesting material, and floor coverings. Furthermore, there is a larger environmental concern as laboratories, zoos, and wildlife reserves work to preserve endangered species.

Presently, infection control is provided through injections, skin surface applications, or through agents taken by mouth. A novel immunization method is described herein that involves introducing pathogens inactivated by UVC into animal environments by providing those environments with inactivated pathogen. In one embodiment, the pathogen can be introduced in an object. Exemplary objects can include nesting materials, food, floor coverings and other objects that can be placed in an enclosure with birds or animals to be treated.

In a pathogen with a one antigen fragment vaccine on the top surface and a vaccine with four antigens on the bottom surface, it may be difficult to specifically target the pathogen because pathogens continuously mutate, and when the focus of the single antigen/antibody attack on the pathogen is mutated, a new variant is created with vaccine evasion.

However, if the vaccine has four antigens even if the pathogen matches a first antibody, it will not create a new, evaded variant because the other three antibodies will kill the newly mutated ineffective variant. While the mRNA vaccines provided a quick approach to providing a relatively safe COVID-19 vaccine, the inventor urges the scientific community to consider the fact the SARS-COV-2 virus that caused COVID-19 has four structural proteins, sixteen non-structural proteins and about nine accessory proteins. The mRNA vaccine was created using just one of the four structural proteins, the spike protein, as the antigen. In comparison the immunity from natural infections or a live attenuated vaccine can have multiple structural protein antigens and possibly some other protein antigens as well. Thus, the approach of continuing to develop vaccines to attenuated viruses should continue to be thoroughly investigated.

Accordingly, according to an embodiment, the inventor is proposing a multiple-antigen vaccine (such as, a four-antigen vaccine). Since the pathogen has no brain or memory, the mutations will continue looking for a new vaccine evaded variant and, in the process, mutate even the number it had matched. In other words, one, two or three matching mutations to avoid the antibodies will not create a new totally vaccine evaded new variant. In order to be effective, the pathogens have to undergo multiple mutations to evade the antibody attack sites and create a new evaded variant. Therefore, compared to a single antigen vaccine, the protection from a four-antigen vaccine is exponentially greater and not just four-fold.

According to an embodiment, a UVC inactivated pathogen which can preserve some or all of the protein antigen can be a more effective vaccine than conventional mRNA vaccines. The inactivation involves just the RNA/DNA of the viruses and the resulting otherwise healthy virus is just incapable of replicating. Such viruses can be called "neutered" viruses. A neutered virus in a room can be inhaled by the occupants and they can get immunized without swallowing the vaccine or getting injected. This is, therefore, a true contactless vaccine.

One of the methods to reduce human infection is by controlling the infection among other animals, birds, bats, primates, etc. . . . This can be done by isolating the causative pathogen that has infected these animals, cultivating the causative pathogen, inactivating the causative pathogen with UVC in a UVC inactivation device. One example of a UVC inactivation device is shown in FIG. 1 and passively immunizing domesticated animals.

Since most farmers, ranchers, and dairymen cannot afford to build and maintain controlled enclosures for all of their animals, it is advantageous to provide methods for passively immunizing animals, domesticated and wild, against certain identified pathogens.

The present invention relates to a novel "contactless" method for infection control. In one embodiment, the present invention discloses a novel method of diffusing an object, such as, floor covering, nesting materials, or food supplies with a neutered pathogenic source.

According to an embodiment, a UVC inactivation device, as illustrated in FIG. 1, has a feeding port 102 allowing an input of the cultivated causative pathogen. The airflow input of a known quantity of the cultivated causative pathogen is sent through one or more UVC channels 104 where the causative pathogen is exposed to UVC. After passing through the one or more UV C channels, the UVC treated pathogenic airflow is pumped using an air pump 106 into a test chamber 108 to be tested for virility. Once the pathogen in the airflow is shown to be inactivated, the inactivated pathogenic airflow is sent through an exit tubing 110 into an enclosure containing an object, such as, pulverized nesting materials, floor covering, or food. These pulverized materials are infused with the inactivated pathogen. These materials are then placed in animal environments, such as hen-houses, dairy barns, or barn stalls to passively immunize these animals.

By infusing floor coverings, bedding, and food sources with inactivated pathogens, the embodiments of the invention can not only be used to immunize domesticated animals but also animals in the wild. For example, many of the diseases that come from the wild that cross over to human populations are from birds or primates. One major source can be bats. Most bats are insectivores. There are thousands of bat species worldwide with varying diets depending on their size and the climate they live in. Small bats (microbats) are mainly carnivorous and eat insects, fish, small animals, amphibians, and reptiles. Large bats (megabats) are mainly frugivorous eating fruits, seeds, leaves, nectar, pollen, and insects as a supplement. By injecting or infusing fruits, seeds, or hay with inactivated pathogens and then provide to animals in the wild, it can be possibly to inoculate those animals in a contactless manner. In another exemplary embodiment, enclosed animals such as mice or rats can be immunized in the aforementioned enclosure (for example) and then released in the wild to indirectly inoculate reptile populations, some bats, and canine and feline populations.

The embodiments of the present invention may serve as an alternative to sacrificing large populations of cattle, chickens, etc. and can save lives as well as money. For instance, an avian flu outbreak has been reported in the United States of America as of Jan. 4, 2024 and about 1 million chickens have been euthanized. This infection can been shown to cross over into dairy herds, and then rarely into humans. Similarly, in April of 2009, Egypt killed all its 300,000 pigs to control swine flu. The humane slaughter association helps to determine when cattle, sheep, goat, pigs, deer, and poultry need to be subjected to emergency killing to prevent spread amongst them as well as spread to the humans. Such widespread slaughter of domesticated animals causes economic hardships in addition to other problems.

Figure 2:
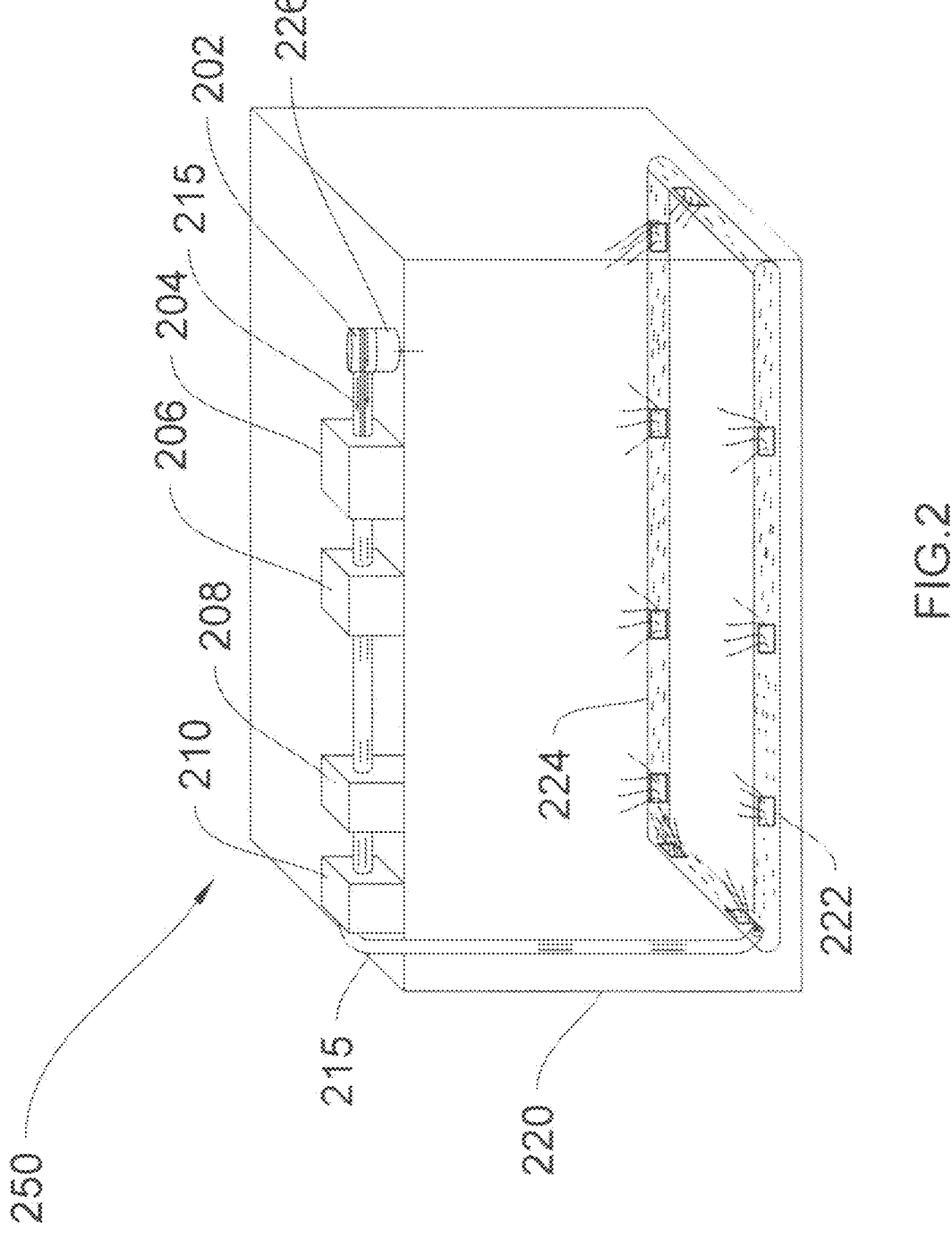
FIG. 2 illustrates an embodiment of an air delivery system.
Figure 7:
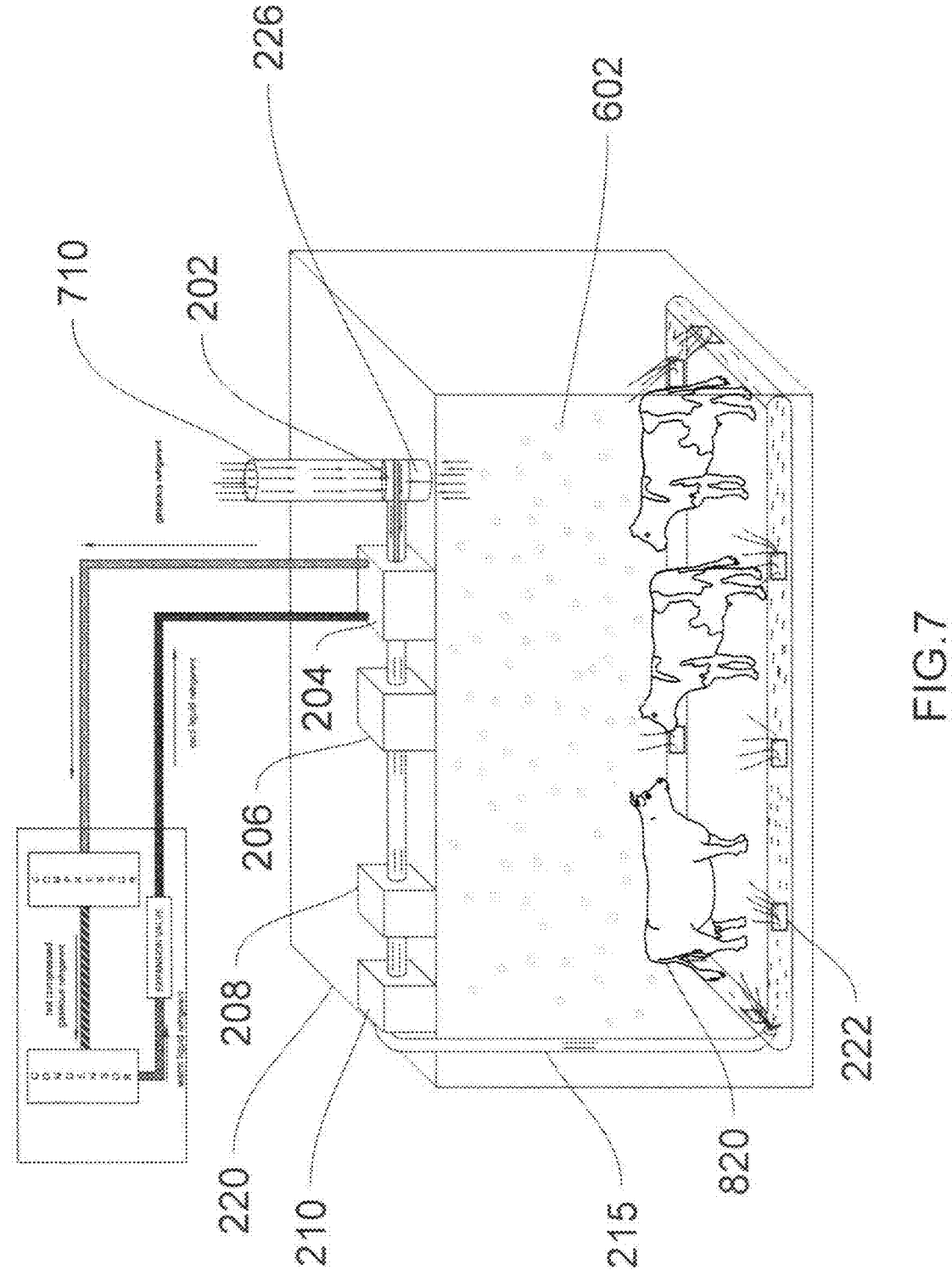
FIG. 7 illustrates a number of cows within one embodiment of an immunization enclosure where an air delivery system circulates air laden with inactive pathogen from an enclosure entry vent to an enclosure air discharge vent.
Figure 8:
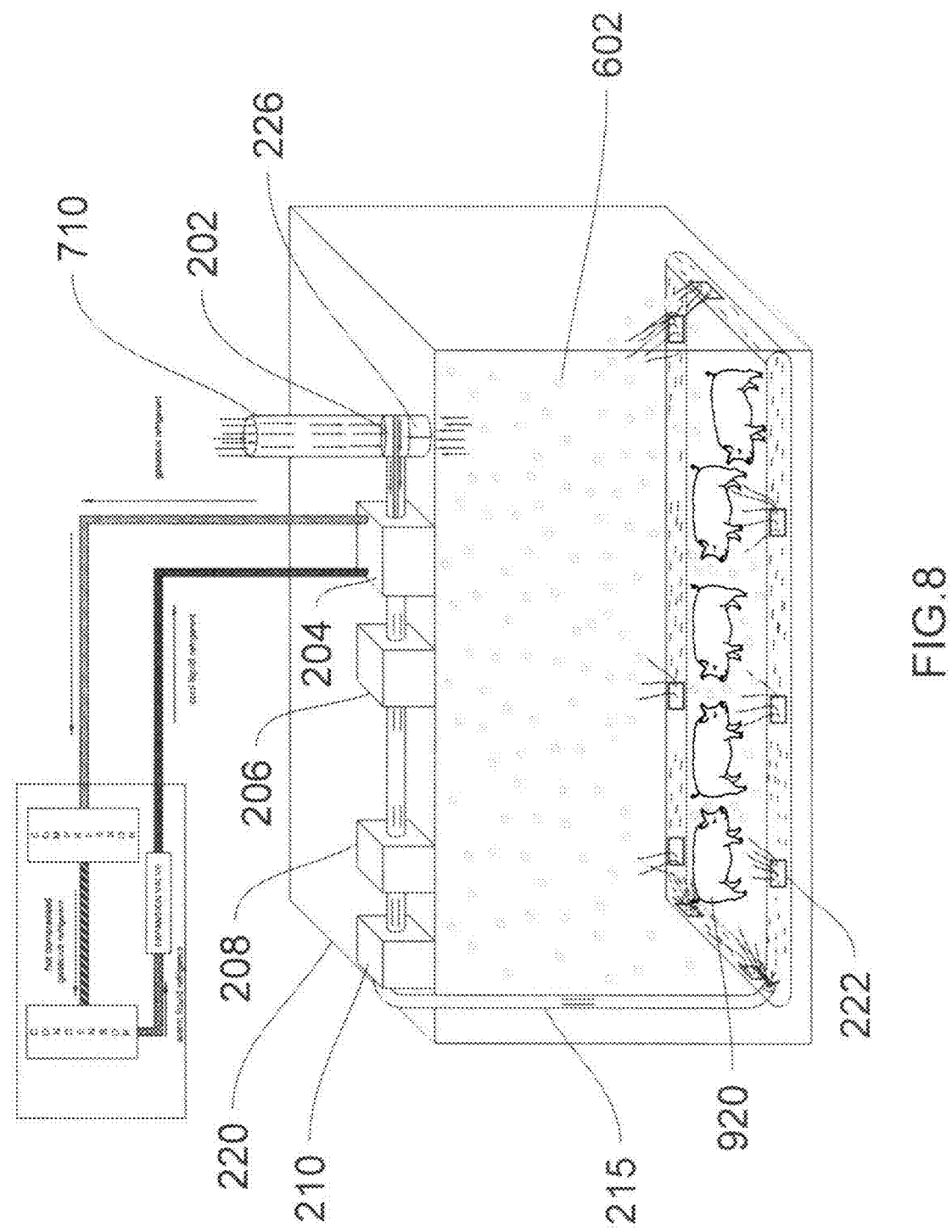
FIG. 8 illustrates a number of pigs within one embodiment of an immunization enclosure where an air delivery system circulates air laden with inactive pathogen from an enclosure entry vent to an enclosure air discharge vent.
Figure 9:
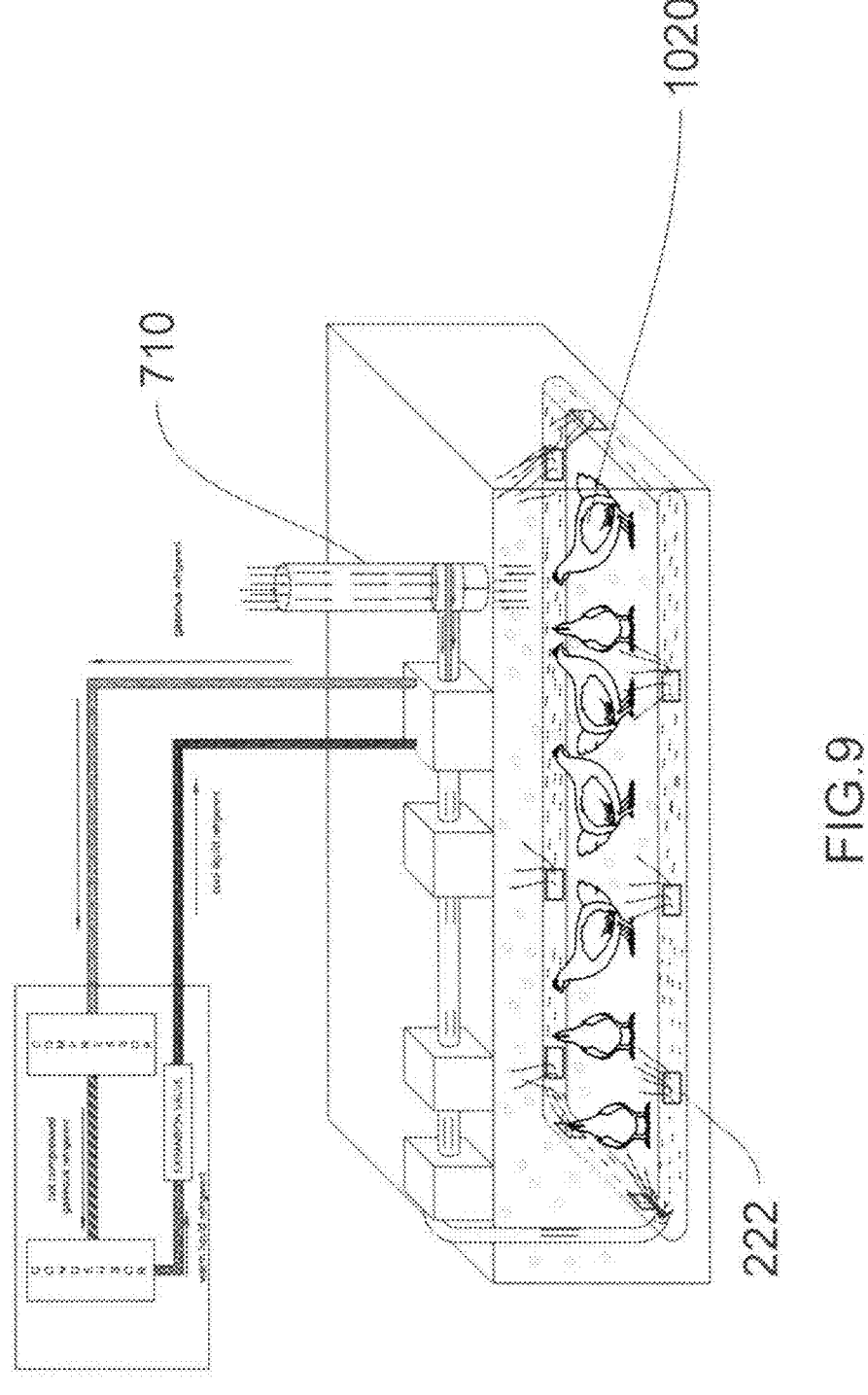
FIG. 9 illustrates a number of chickens within one embodiment of an immunization enclosure where an air delivery system circulates air laden with inactive pathogen from an enclosure entry vent to an enclosure air discharge vent.

One embodiment of the present invention includes an air circulation and delivery system 250 that delivers UV C treated air to an enclosure with a controlled air flow of air containing an inactivated pathogen for inducing a passive immunity in birds or animals breathing in the inactivated pathogen within the enclosure (see FIGS. 7-9). A schematic illustration of the enclosure is shown in FIG. 2. The enclosure 220 has an enclosure entry vent 222 through which UVC treated air enters the enclosure, circulates throughout the enclosure, exits through the enclosure discharge vent 226, and is re-circulated after loading the pathogen and neutering the pathogen. The air entering the enclosure 220 is an air source that initially enters an air intake 202 and then passes through an air circulation pathway 215 to an air conditioning unit 204, an air mover 206, a UVC disinfection unit 208, and then into the enclosure through one or more enclosure entry vents 222. Multiple enclosure entry vents may be connected to each other via an entry vent circulation pathway 224. The air source may be passed through a test chamber 210 after it passes through the UVC disinfection unit 208 to ensure Sterility Assurance Level (SAL). The test chamber 210 allows the collection of samples to ensure absence of any active pathogens.

Another embodiment of the present invention includes a system for immunizing birds and animals (such cattle 820, pigs 920, or chicken 1020) with an inactivated or neutered pathogenic source. Other embodiments include a method of providing infection control and immunization by breathing previously "treated" and neutered pathogen-laden air in a closed enclosure.

Figures 4A, 4B:
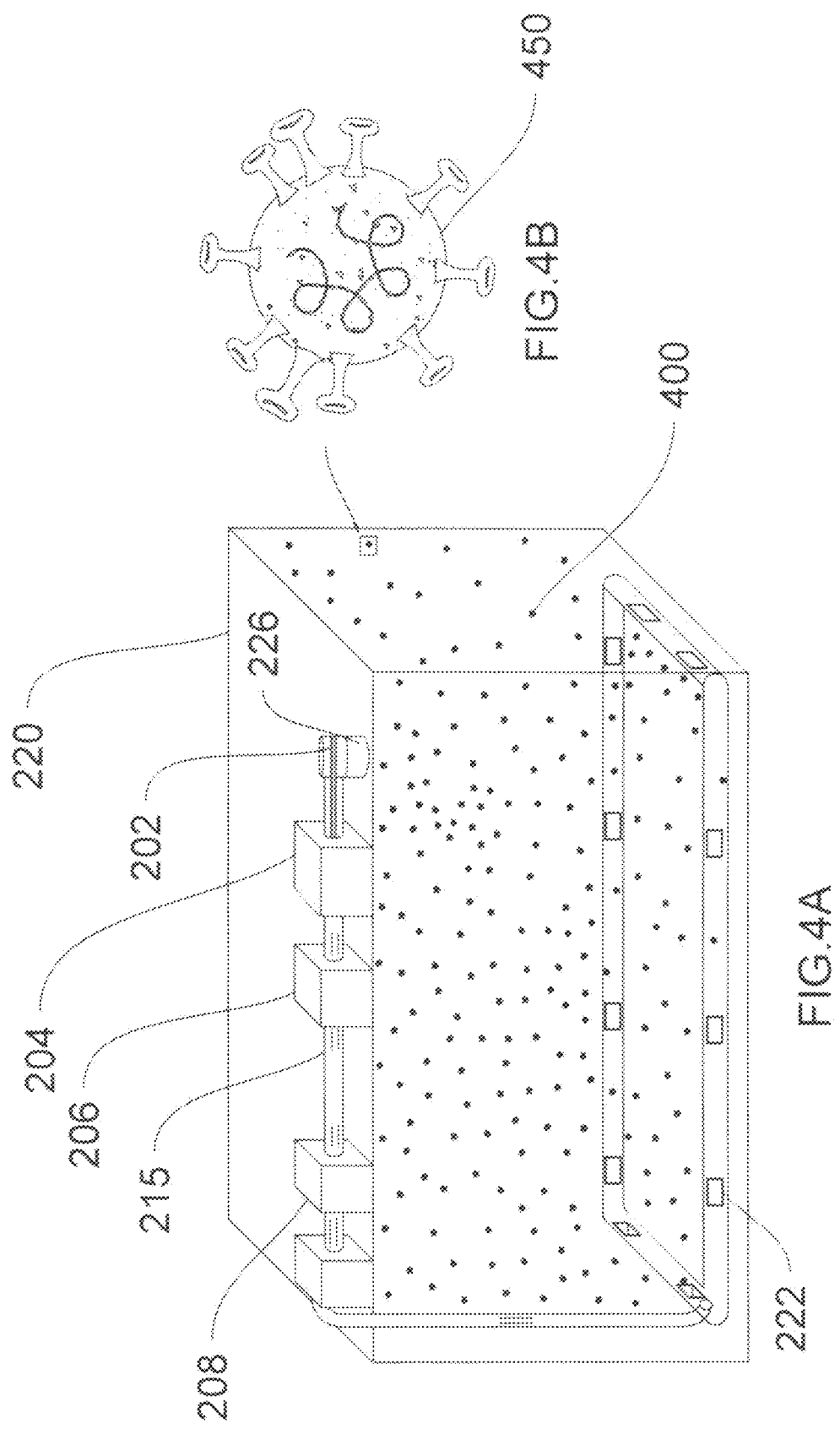
FIG. 4A illustrates one embodiment of the air delivery system shown in FIG. 2 with pathogen-laden air circulating within an embodiment of an enclosure.
FIG. 4B is a schematic illustration of a SARS-COV-2 as an example of a pathogen.
Figure 5:
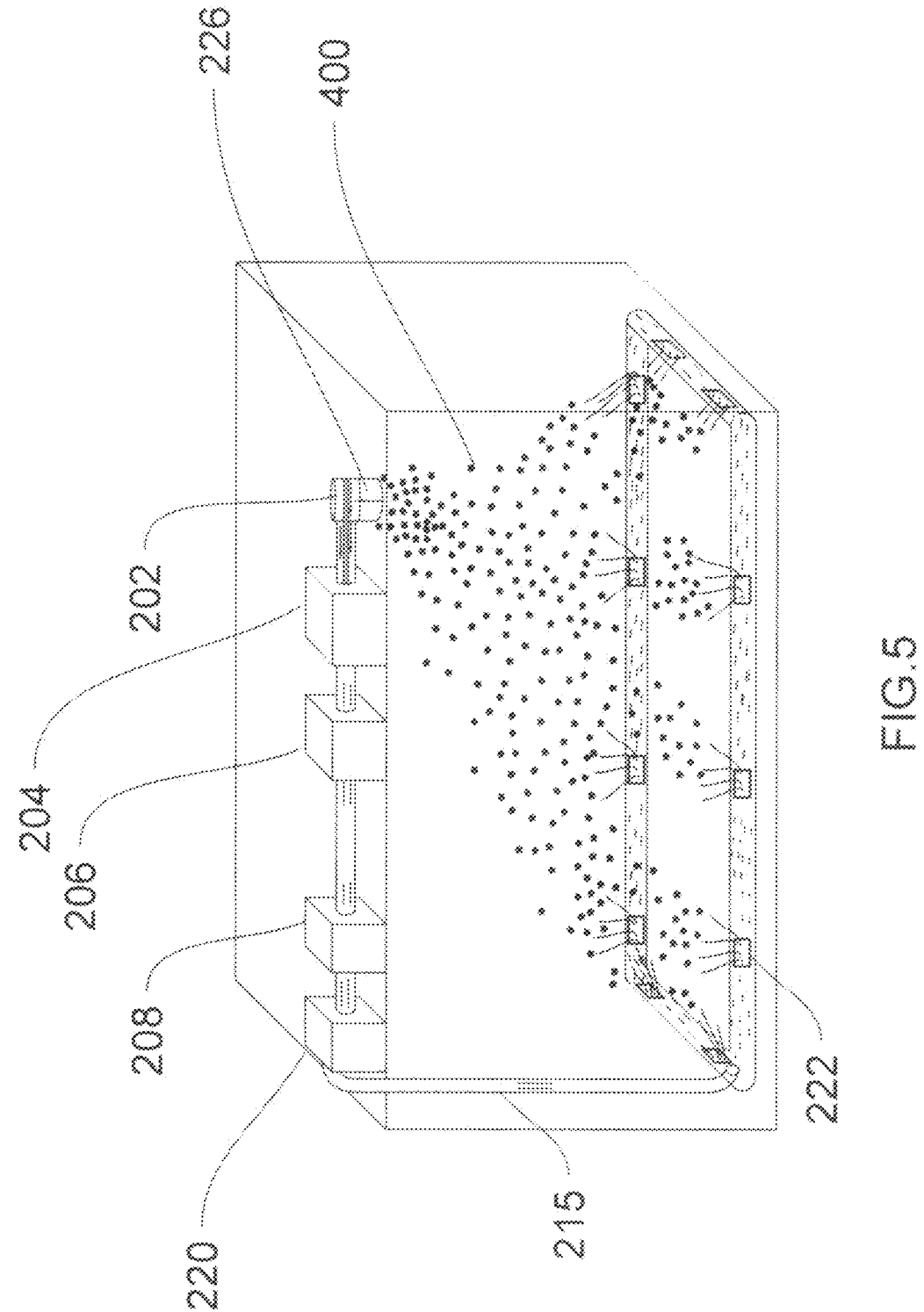
FIG. 5 illustrates one embodiment of an air delivery system showing the air circulation laden with active pathogen in an enclosure going from an enclosure entry vent to an enclosure air discharge vent.

The SARS-COV-2 virus 450, as illustrated in FIG. 4B, is used as an exemplary virus for discussing the embodiments of this invention. According to an embodiment, the SARS- COV-2 virus is passed through one or more UVC disinfection units where it gets neutered (inactivated) and unable to replicate in the cells of the victims. It is also possible for the spikes of the neutered SARS-COV-2 to engage the ACE2 proteins and deny the pathogenic SARS-COV-2 virus a landing site, if the spikes are not deformed or destroyed in the neutering process.

Alternately, immunization enclosures can be created to provide the same kind of protection to birds and animals. Here also, the animals sitting in or moving around in such enclosures will get immunized by just breathing the treated air containing neutered pathogens with one or more antigens. Typically, such enclosures will have a pathogen loading inlet 710 where a predetermined quantity of pathogen (i.e., the pathogen load) is injected into the system and taken through an air conditioning unit followed by a UVC disinfection unit which inactivates or neuters the pathogen without destroying its antigenic proteins/peptides. This treated air is then routed into the enclosure where one or more animals are immunized.

Air Conditioner System

As used herein the term "air conditioner system" or "air conditioning system" refers to a system that controls the temperature of the air leaving the system. The temperature is typically controlled by a thermostat. An air conditioner system may include both a cooling mechanism and a heating mechanism.

A schematic of an air cooling unit of the air conditioner system 204 is shown in FIG. 7. A refrigerant enters the cooling unit through an air pathway 702. The compressor 704 of the cooling unit compresses the refrigerant vapor and moves it towards the condenser 706. The heat of compression raises the temperature of the refrigerant vapor causing it to be a high pressure superheated vapor. The condensed refrigerant then moves through the expansion valve 708 that expands the refrigerant reducing its temperature before returning to the air conditioning system.

Air M over

The air delivery system of the present invention relies on an air mover 206 or air circulator, such as an air pump or a fan, to ensure a controlled rate of air flow through the air delivery system. The rate of air flow through the system is important to the operation and efficiency of the system.

UVC Disinfection Unit

Figure 3A:
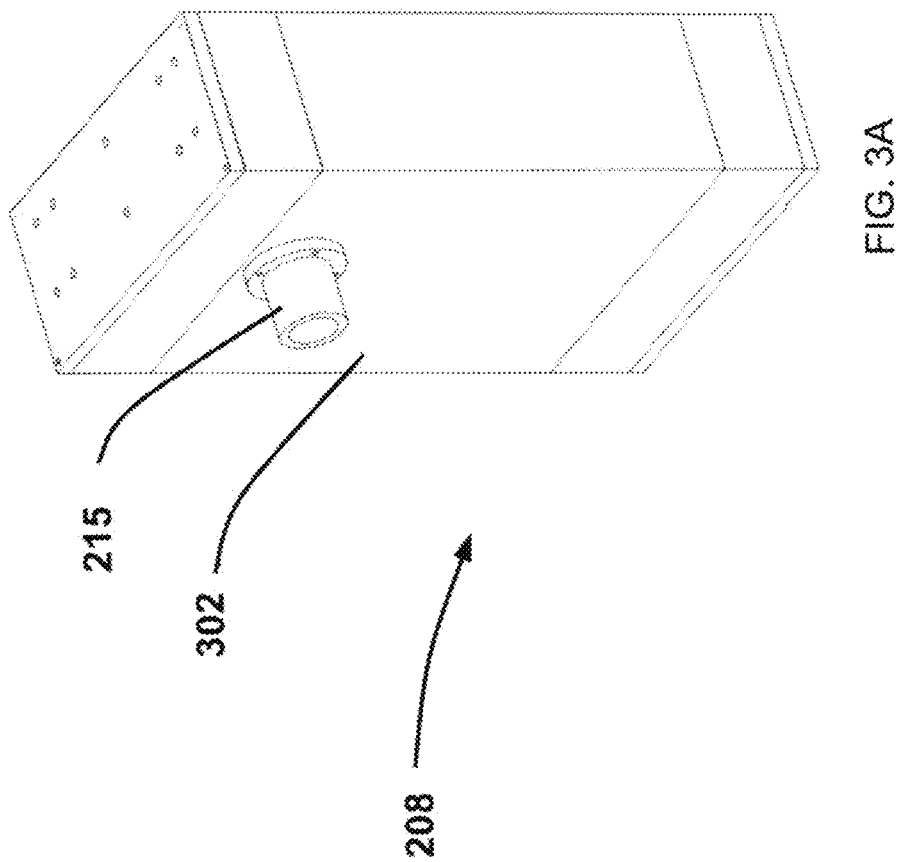
FIG. 3A illustrates one embodiment of a housing of a UVC disinfection unit.
Figure 3B:
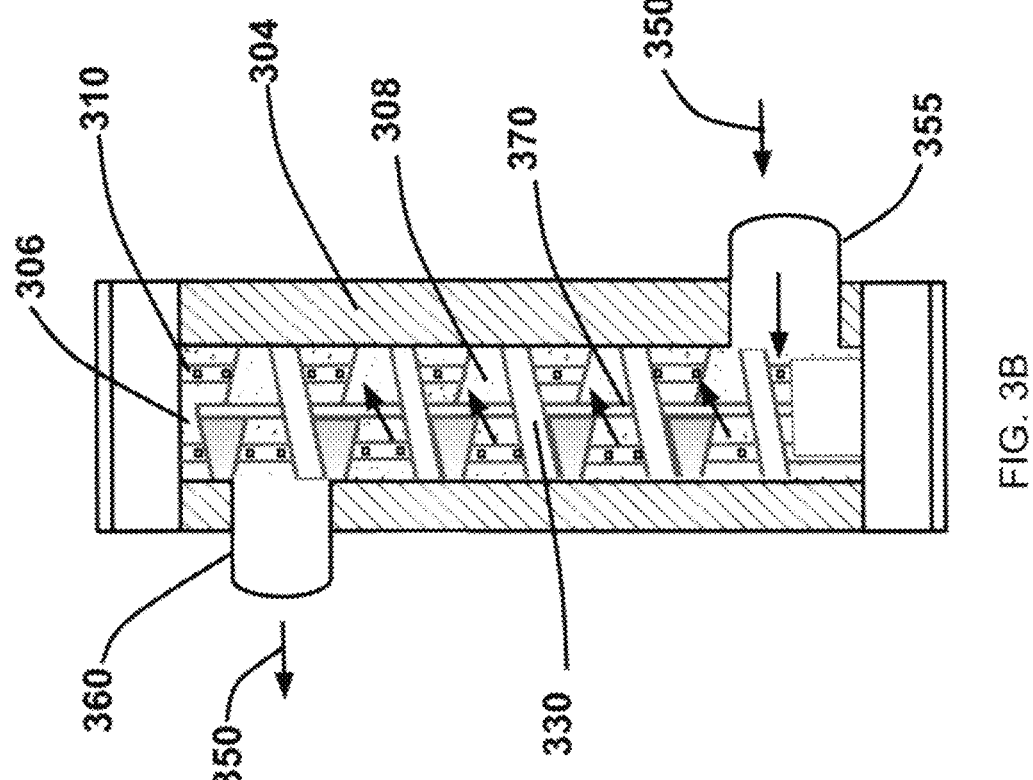
FIG. 3B illustrates an embodiment of a disinfectant chamber of the UVC disinfection unit illustrated in FIG. 3A.

One embodiment of a UVC disinfection unit 208, illustrated in FIGS. 3A-3B, has an opaque housing 302 containing one or more disinfectant chambers 306. The disinfection chamber has a chamber wall 304. The housing 302 may serve as the chamber wall, if the UVC disinfection unit 208 contains only one disinfection chamber 306. However, the chamber wall may also be UVC transparent as is often the case when the UVC disinfection unit contains more than one disinfectant chamber 306. Each chamber has a chamber inlet 355, a chamber outlet 360, and a centralized inner bore/stem 370 having an interior chamber surface 308 facing the inner bore; a UVC light source 310 positioned adjacent the interior surface; and a helical air flow diverter 330 centralized within the inner bore proximal to the UVC light source, wherein the helical airflow diverter creates a helical airflow path 350 for the air flowing through the chamber.

Each chamber will have at least one UVC light source 310 and a helical air flow diverter 330 as described above. The chamber inlet 355 allows the incoming air to enter the disinfection chamber at one end of the helical air flow diverter 330 and circulate around each rung of the helical air flow diverter until the outgoing disinfected air exits out the air outlet 360. Typically, the helical air flow diverter fills most of the empty space in the disinfection chamber thereby creating an air flow path that circulates around each helical rung in a narrow space between the disinfection chamber wall 304 and the helical air flow diverter rungs. Thus, as the air flows from the inlet to the outlet, it circulates close to the UV C light source(s) throughout the disinfection chamber(s). The particles including the pathogens in the air are driven very close to the UVC source due to the centrifugal force.

The helical air path through each disinfection chamber 306 will extend the time that the air is exposed to the UVC light sources. The time the air spends in the disinfection chambers is further controlled by the speed of air movement through the chambers as controlled by the air mover 206. The air mover controls the movement of the air through the air disinfection units. The air mover functions at different power levels that can be electronically controlled. By altering the power level of the air mover, the air circulation can be made faster or slower. The velocity of the air flow through the disinfection unit(s) will proportionately increase or decrease the dosage of UVC encountered by any pathogen in the air flow through the disinfection unit(s).

Ultraviolet Inactivation of Pathogens

UVC light is a well-known disinfectant. Many UVC light emitting devices are available in the marketplace. These devices are used to "sterilize" surgical suites, airports, and other such spaces. However, for effective disinfection, the UVC light has to be strong enough to destroy the microorganisms within a close proximity. Additionally, the microorganisms have to be exposed to the UVC light for a sufficient duration of time before they are neutralized. Such high energy UVC radiation and long exposure to UVC radiation can injure normal human cells like skin, cornea, and other cells. Therefore, UVC light should not be allowed to come near hands, face or other areas of the skin. Furthermore, exposure of the skin to UVC radiation can cause skin irritation and other ailments.

UV light is an electromagnetic radiation beyond the wavelength of the visible violet or beyond the spectrum that the human eye can see. The UV light itself has a spectrum ranging from 100 nanometer to 400 nanometers. UV light having wavelengths from 315 nm to 400 nm is called UV-A, from 280 nm to 315 nm is called UV-B, and from 200 nm to 280 nm is called UVC. Far UVC light has a spectrum ranging from 207 nm-222 nm. For the purposes of this application, the terms "UVC" and "far UVC" are used interchangeably.

The earth's ozone layer blocks the UVC but allows UV-A and UV-B to reach earth. The shorter the light wavelength is, the less it will penetrate human skin. UV-A and UV-B can damage human skin and are the ones implicated in sunburn, skin cancer, and an increased risk of cataracts. UVC from the sunlight cannot normally reach the earth because it is filtered out by the earth's ozone layer. Far UVC and UVC light penetration into the skin is low, but is sufficient to cause some major damage due to the high energy level. However, UVC light in the appropriate dosage penetrates microorganisms and denatures their RNA and/or their DNA, making the reproduction of those microorganisms impossible.

The kill rate of UVC light depends on the specific microorganism you are trying to destroy as well as the UVC dosage the organism receives. Dosage (J/m2) is a combination of exposure time and intensity (microwatts per square centimeter). $UV\_dose = UV\_bulb\_power * Exposure\_time / (4*pi*UV\_bulb\_distance^2)$. The intensity is a measure of the power of the UVC and its proximity to the organism, where Intensity, $E = UV\_bulb\_power / UV\_bulb\_distance^2$.

There are numerous ways to control the delivery of ultraviolet light to pathogens. One controllable delivery method is to employ one or more embodiments of the unique UVC disinfection unit 208 described below.

UV Light Source

The number, type, strength and the placement of the UVC lights 310 in the disinfection chamber 306 will ensure that all microorganisms such as bacteria and viruses in the air flow passing through the disinfection chamber will receive a sufficient UVC dosage to kill any microorganisms in the air. Likewise, the number, type, strength and the placement of the UVC lights in each disinfection chamber 306 will ensure that the bacteria and viruses in the air flow passing through the disinfection chamber will receive a sufficient UVC dosage to disinfect the air flowing through the device.

The UVC light source 310 can be any type of UVC light source, such as the UVC tubes or the UVC light strips. UVC light sources may include mercury lamps, fluorescent tubes, pulsed xenon lamps, excimer lamps, UVC LEDs, and UVC lasers. Once the UVC light source is selected and the wattage or irradiance is known, the exposure time to achieve the desired dosage can be calculated and the appropriate time for the air path to spend passing through the disinfection chambers in close proximity to the UVC lights can be determined. In fact, when more than one disinfection chamber is used, different UVC light sources may be used in the different chambers. Different UV light sources may be selected for the different wavelengths that they produce, their different intensities, their different lifespans, the difference in their heat production, or for any other reason.

Controlled Dosage

The UVC air disinfection unit described above is a reliable means of delivering a set dosage of UVC to a pathogen in an air supply that passes through the unit. The dosage can be varied by controlling the intensity of UVC put out by the UVC source(s), the number and position of the UVC sources, the number of disinfection units and/or the number of disinfection chambers per disinfection unit. The dosage can also be varied by controlling the exposure time by varying the air flow velocity through the disinfection unit(s) or controlling the length of the air stream pathway through the unit. Examples of other variations include: varying the strength of the UVC sources, varying the proximity of the microorganisms in the air flow to the UVC sources, varying the distance traveled by the air stream, and varying the time and proximity that the air stream is exposed to the UVC light sources in the disinfection chambers 306 within UVC disinfection unit 208.

Quantitating the Damage to a Pathogen

Aerosolized samples of a known quantity of a virulent pathogenic source will be collected before and after UVC treatment in the UVC disinfection unit(s). By choosing the appropriate wavelength of the UV radiation, it is possible to destroy the genetic material of the pathogen (i.e. DNA or RNA) before it destroys any other molecules in the pathogen. A neutered pathogen is defined herein as a pathogen with its genetic material (i.e., its RNA or DNA) destroyed so that it cannot reproduce and yet has some or all of its membrane or structural proteins intact. For instance, a ribonucleic virus can be neutered by destruction of its RNA using UVC in a dose related manner. Using a minimal UVC dosage for destroying its genetic material allows the virus to retain its morphology and the structural integrity of its proteins. A vaccine derived from an intact neutered virus can generate antibodies to various antigenic regions available in one or more of the viral proteins.

Using the SARS-COV-2 virus as an example, aerosolized samples collected before and after they are subjected to a set dosage of UVC radiation will be analyzed to compare the integrity of the samples' RNA and proteins to the known structure of the virus' known RNA and capsid proteins using standardized laboratory techniques such as 2D gel electrophoresis. One embodiment of this process sends one aerosolized standardized SARS-COV-2 viral source through each of a variety of UVC disinfection units that vary in the dosage of UVC delivered to the viral source. Samples from each UVC disinfection unit will be collected by an automatic sampling apparatus and analyzed for the integrity of the various viral components such as its RNA and proteins. Current studies show that UVC inactivation is more precise than the overall damage done to the pathogen with detergents, formalin, chlorine and other such chemicals. It is hypothesized that the resulting protein antigen is healthier after UVC neutering compared to the overall mutilation created by other agents. This is very similar to precision bombing with UVC and cluster bombing with other agents.

Numerous samples of the aerosolized standardized virulent pathogenic source will be subjected to gradual increases in UVC dosages or subjected to UVC of different wavelengths. With each incremental dosage increase or different wavelength the UVC treated pathogenic source will be collected and analyzed for any damage to the genetic material and/or proteins and compared to the untreated pathogenic source. Thus, any damage to the genetic material and/or proteins of the pathogenic source can be correlated to increases in the UVC dosage used or variations in the wavelength of the UVC to treat the pathogenic source. For example, any damage to the genetic material and/or proteins of a standardized SARS-COV-2 source can be correlated to increases in the UVC dosage of 254 nm used to treat the SARS-COV-2 virus or one with the UVC 222 nm or any other wavelengths. This information can be used to devise a method of neutering the COVID-19 virus without destroying its structure, including the nucleocapsid protein or its envelope proteins (the M protein, E protein and S protein). If the spike morphology is retained after UVC treatment, then it will continue to be able to engage SARS-COV-2 $ACE_2$ receptors and competitively inhibit the untreated virus's ability to engage the same $ACE_2$ receptors.

Other embodiments will vary the UVC dosage given to an aerosolized standardized SARS-COV-2 viral source by sending the viral source through a series of disinfection units that vary in the number or type of their UVC sources and/or disinfection chambers, or by sending the viral source through the disinfection unit(s) at different velocities or flow rates. The dosage of UVC delivered to the viral source is calculated and the degree of damage to the virus is quantified from samples collected by an automatic sampling apparatus and analyzed for the integrity of the various viral components such as its genetic material (RNA or DNA) and its proteins.

Immunogenic Compositions

The present invention includes a process for producing an immunogenic composition. An immunogenic composition as defined herein is a neutered/inactivated pathogen that retains at least one antigenic determinant available for binding. The process comprises standardizing a known quantity of a virulent pathogenic source; determining the degree of ultraviolet inactivation of the pathogenic source required to neuter the pathogen while retaining the integrity of at least one antigenic determinant; preparing an immunogenic composition to produce or increase the animal or bird's immunity to the inactivated pathogenic source.

One embodiment of the present invention is a process for destroying the RNA or DNA of a pathogen, such as a virus, using germicidal UVC radiation. For instance, the SARS-COV-2 virus can be neutered by destruction of its RNA using UVC in a dose-related manner. This allows the virus to retain its morphology and the structural integrity of its nucleocapsid and envelope proteins. To date, the major SARS-COV-2 vaccines have been prepared to create antibodies to one or more portions of the S protein. However, the S protein has multiple domains. For example, if the vaccine is made only against the Receptor Binding Domain (RBD) of the S protein, the antibodies produced are only against one or two peptide portions of the S protein. As the virus continues to mutate, one or more of these mutations will eventually overcome this R BD vaccine.

Viruses rapidly reproduce in infected cells and often at least a few of the released virus particles will have mutated. Over time some of these mutations may be able to evade the antibodies made to an attenuated virus or to a portion of a protein used as an antigen in a vaccine. For example, SARS-COV-2 is an RNA virus. Typically, the SARS-COV-2 virus will try to evade the antibodies produced by a vaccine to one or more antigens used in producing the vaccine. However, the SARS-COV-2 has three envelope proteins and the nucleocapsid protein around the RNA. If each of these proteins generated one or more antibodies, then it would be harder for the virus to mutate enough to avoid all of the antibodies produced. The mutation of the virus to evade all of the antibodies produced to a variety of proteins will be difficult. This is because mutation is sustained and propagated only through progeny. If the mutation does not generate progeny, that particular mutation is discarded. In time, the virus will continue to try and mutate, but will then have to stop. Thus, vaccine evasion by a multi-mutated virus will be significantly reduced. Efforts to produce inactivated whole virus vaccines against SARS-COV-2 have met with poor success. It is hypothesized here that the low success rate with this inactivated whole virus vaccine was because the conventional inactivation techniques mutilate the antigens to variant degrees. The UVC-neutered antigens will be more effective.

A vaccine derived from an intact neutered virus can generate antibodies to various antigenic regions available in one or more of the viral envelope or capsid proteins providing a full spectrum of antigens capable of eliciting a full spectrum of antibodies. For example, SARS-COV-2 has several envelope proteins—the spike protein (S protein), the membrane protein, and the envelope protein in addition to the nucleocapsid protein; wherein each of these proteins can potentially independently elicit specific antibodies to one or more antigenic regions in each protein.

If antibodies are generated to antigenic regions of more than one protein, then a viral mutation to circumvent one particular antibody might remain unmutated while it tries to mutate against another antibody. For a successful mutation the virus will have to mutate against all four antigens simultaneously and this can frustrate the system. For any mutation to prevail and propagate, it has to have successful progeny. If the partial mutation does not produce progeny that particular mutation is usually discarded. In other words, not all mutations result in a new variant. In time, the virus will continue to try and mutate but will then have to stop. Thus, vaccine evasion by the virus can be significantly reduced. A reduced rate of mutation will naturally occur through a reduced rate of infection.

SARS-COV-2 virus cannot multiply or mutate in the air but must mutate in infected cells. By blocking the entry of the virus into our bodies, the rate of mutation is automatically eliminated or reduced. The polyvalent vaccine has a better chance to do this. With four types of antibodies evading, the chances are exponentially lower than with just one type of antibody. This is like a burglar trying to unlock four locks on a door at the same time. With any luck, the burglar will keep locking and unlocking the four locks randomly and will never get all the four unlocked at the same time. The polyvalent vaccine can provide a similar challenge to the virus. Partial S protein antibodies are even easier to evade by mutation. Imagine an S protein-lock has seven levers. The mutations have to cover all seven. If the antigenic determinant(s) are only a small part of the S protein, the antibodies produced are only against a few of these seven levers. This makes the mutation much easier.

For example, the simplest form of UVC damage to the SARS-COV-2 virus damages only the RNA leaving the envelope (capsule) and all its four proteins preserved. It is unlikely that all four proteins have the same threshold for destruction by UVC. The same is true for the structure of the envelope itself. After determining the gradation of sensitivity for destruction of viral components by UVC, one may predictably produce different levels of SARS-COV-2 damage such as RNA damage with all four proteins preserved, RNA and one protein damaged with three proteins preserved, RNA and two proteins damaged with two proteins preserved, and RNA and three proteins damaged with only one protein preserved. A vaccine can be produced from any one of these graded options and that vaccine can be tested for diverse antibody production and their risks and benefits. Thus, an educated selection can be made of which damaged virus should be included in an inoculum or vaccine. Theoretically, the first option with all four proteins preserved will have more advantages than the others provided this vaccine has no increased risk to the recipient.

The development of polyvalent neutered whole virus vaccine can be explained using SARS-COV-2 as an example. This virus has positive-sense, single strand, RNA combined with nucleoprotein as its core. This type III virus has an envelope made of two main proteins, the M (for membrane or matrix) and E (for envelope) and an "attack" protein projecting out and appropriately called the spike protein. By utilizing two-unit systems, to produce predictable, graded, optimal damage to the virus, it should be possible to produce four types of antigens. The lowest dose of UVC can just neuter the SARS-COV-2 by denaturing the RNA without damaging the architecture of the virus or the four proteins. The UVC damage is so precise that it can destroy the RNA while preserving the nucleocapsid protein that is in close association with the RNA like in a braided cord. This product will have four potential antigens from the four preserved proteins for creating a broad-spectrum antibody reaction. By increasing the strength and duration of the UVC and the proximity of the virus to the UVC right inside the first chamber/unit, a second possible product will be a neutered virus with one damaged protein. It will not be difficult to measure the sensitivity of the four proteins to UVC, and by using appropriate dose of UVC the viral antigen can be with four proteins, three proteins, two proteins and just one protein. For instance, the first housing can have UVC of wavelength 254 nm which is absorbed heavily by the nucleic acid and will be good for neutering the virus. The second housing can have UVC of wavelength 222 nm which is absorbed heavily by the proteins. Grading of the protein damage can be accomplished by adjusting the UVC 222 dosing in the second housing.

Since the RNA is denatured in all four of these products, the resulting whole virus cannot be multiplied in any cell and is not infective. It is difficult to predict which of these four UVC damaged viruses will make the optimal vaccine. This has to be determined with animal experiments and a determination of risks versus benefits. Common sense dictates that the neutered virus with four antibody-producing proteins will be the best vaccine. In this situation, the virus will have to create mutations against all antibodies at the same time to evade the vaccine. Mutations are "errors" produced during virus multiplications in the cells (accidental, evolutionary, random or other mechanisms) but not calculated or intentional. The more viruses in circulation, the more the chances for mutations. Such mutations take place in each infected animal or bird through each virus multiplication cycle. At the peak of COVID-19, the estimated number of mutations generated daily in the world was about 100,000 to 1 million.

According to the inventor, a neutered SARS-COV-2 virus is like a defanged cobra. A defanged cobra can crawl into crevices and get into a house, but it cannot hurt the inhabitants without its teeth. Likewise, the neutered SARS-COV-2 virus, that retains its morphology, will invade the animal or bird cells through the same A CE2 entrance gates. Then, the neutered SARS-COV-2 virus would die with no progeny. Additionally, the undamaged proteins released by the dead virus can provide foreign antigens that the body can generate antibodies against. These antibodies can then attack and defeat any future active virus invasions. The multiple antibodies produced against different components of the virus can react with the virus and negate its ability to reproduce and cause illness. Furthermore, the virus will struggle to overcome these multiple protein antibodies. Using a specialized pathogen-killing or pathogen-taming system, vaccines of these four grades can be created. The predictable graded destruction of the pathogens will facilitate the development of reliable and optimal vaccines.

A neutered, inactivated live virus vaccine provides the benefits of live vaccines without the risk of the animal or bird getting infected. The neutered SARS-COV-2 vaccine is better than inactivated whole virus vaccines as it does not have any side effects from the agents used to inactivate the virus. Also, the virus and its capsid or envelope proteins are not mutilated in the process of neutering it, unlike in the process of inactivating the virus using other methods. The UVC treated neutered non-mutilated SARS-COV-2 virus behaves like the whole virus in its antigenic potential without any side effects and without causing any infection by accident.

Delivering Immunogenic Compositions

Embodiments of the present invention include methods for immunizing birds and animals with an inactivated or neutered pathogenic source. One example of a neutered pathogenic source may be a SARS-COV-2 virus that is neutered with a defined dose of UVC light. Presently, immunizations are provided through injections, inhalants, skin surface applications, or through agents taken by mouth. The present invention discloses a method of providing infection control/immunization passively, that is through contactless means, by merely breathing in an inactivated or neutered pathogen having exposed antigens. The antigens enter the recipient's air passages and body through normal breathing. The recipients that breathe in the inactivated pathogen with its antigens exposed will make antibodies to various antigenic determinants within those exposed antigens.

Figure 6:
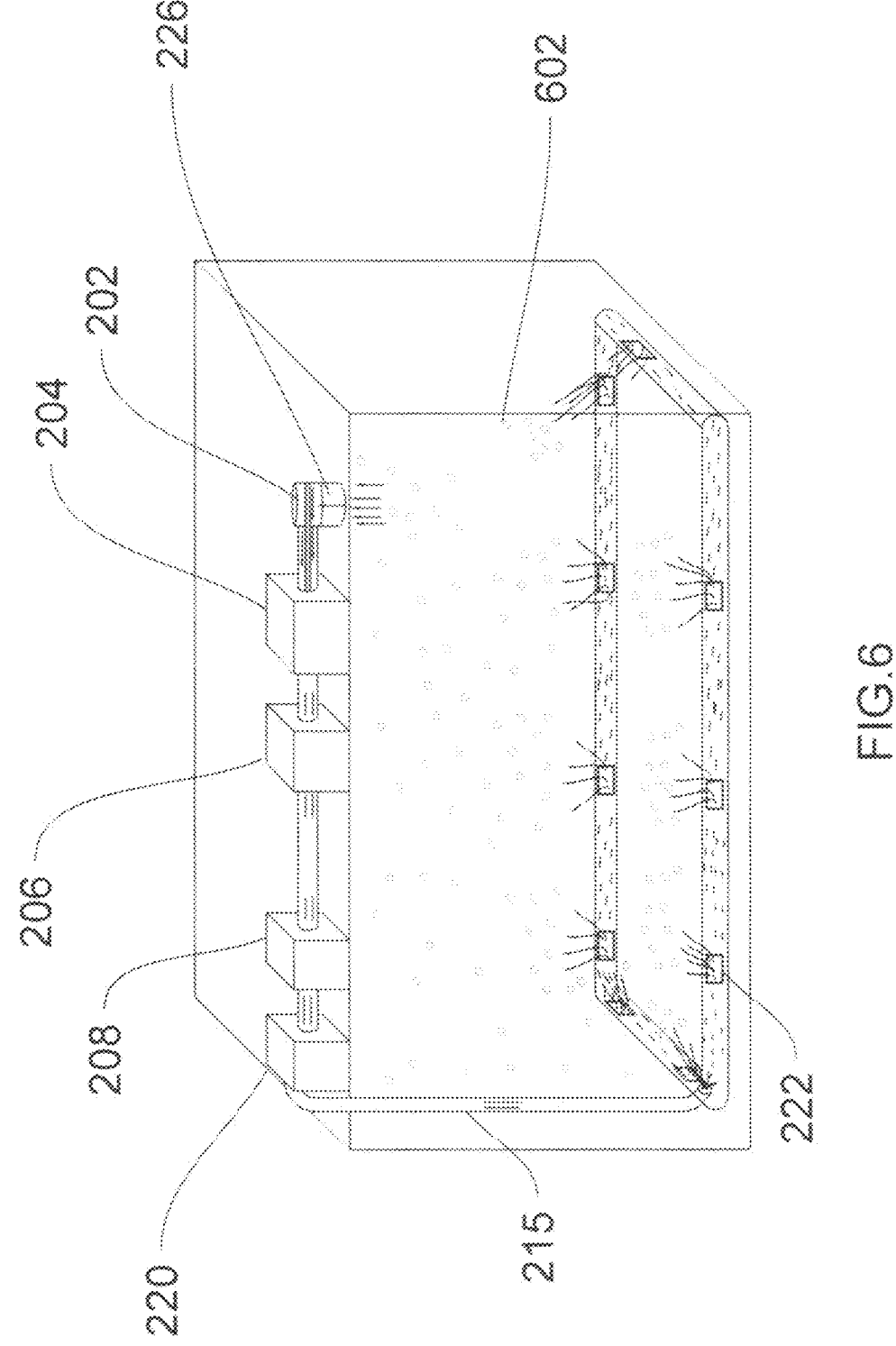
FIG. 6 illustrates one embodiment of an air delivery system showing the air laden with inactive pathogen in an enclosure going from an enclosure entry vent to an enclosure air discharge vent.

Inactivated pathogens 602 having their antigens exposed may be presented to a bird or animal via a previously "UVC treated" ambient air in a closed room or a confined environment 220 such as shown in FIG. 6. As described herein, the UVC treatment of air involves the inactivation of pathogens in an air source. The pathogens may be those intentionally introduced at a precalculated dose, or those from viruses or pathogens released into any given air source by animals that have shared that air source.

Advocates of inhalation vaccines, such as those described herein, have highlighted that they promote both a mucosal immune response as well as a systemic immune response. A vaccination that is introduced by normally breathing treated air is easier to dispense and more likely to be accepted as they will not cause patient discomfort.

For example, SARS-COV-2 virus enters the body through the upper airways and spreads to the rest of the body. More specifically, the rear two thirds of the nasal passage is known as the landing place for this virus. This is why one swabs the rear portion of their nasal passage for a proper diagnosis of this virus. By providing a vaccine that can be inhaled and deposited along of the nasal passage, the attack on the virus is focused at its first landing place and will be more effective. This will also ensure that the neutered and artificially created "pseudo virus" will engage all the $ACE_2$ entry points on the host cells making the true virus particles lost in the wilderness with no $ACE_2$ entry points in the upper respiratory tract.

COVID-19 researchers have attempted to improve the systemic immune response and the mucosal immune response. Advocates of inhalation subunit vaccines have highlighted this as an additional benefit of inhalation vaccines. Promoting both a mucosal immune response and a systemic immune response may be achieved by a total viral protein vaccine and will perform better than the subunit vaccines currently undergoing clinical trials.

Contained Spaces with Treated Ambient Air

Some embodiments of the invention include methods of providing infection control/immunization by merely breathing previously "treated" ambient air in a closed room or a confined environment.

The modified air circulation and delivery system 250 can include a self-cleaning circulation system with one or more UVC disinfection units 208 in the air circulation system. Each disinfection chamber 306 with its UVC lights 310 and helical airflow diverter 330 irradiates the air flowing through the chamber. The air disinfection unit 208 may be configured with various different dimensions as selected to fit the needs of a particular embodiment of an enclosure such as the embodiment shown in FIG. 2. A test chamber 210 is incorporated into the modified air delivery system 250 where one can selectably remove a sample of the treated air to test the sample and make sure that the pathogen is totally neutered and for the presence of available antigenic determinants.

For example, if the SARS-COV-2 virus is taken up into the system 250, the SARS-COV-2 virus is passed through one or more UVC air disinfection units 208 where it gets neutered (inactivated). By titrating the UVC dosage, one or all of the SARS-COV-2 antigens are preserved in this neutered virus population. The load of virus in the ambient air is now inactivated and cannot cause infection when it is recirculated into the enclosure.

As shown in FIGS. 7-9, the enclosure can be provided as a free-standing or stand-alone immunization enclosure to provide immunization to animals. The free-standing enclosure can be conveniently transported to the desired location. In one or more embodiments, the free-standing enclosure can be configured as a mobile or transportable unit.

As shown in FIGS. 7-9, the free-standing enclosure can be configured to provide protection to one or more animals against specific viruses or pathogens within those enclosures. This arrangement can be used to immunize cattle (FIG. 7), pigs (FIG. 8), birds (FIG. 9) or other animals. Here, the animals sitting in or moving around in such enclosures will get immunized by just breathing the air in the enclosure. Such enclosures may be modified to include multiple enclosure air entry vents 222 at various heights and various locations to ensure adequate circulation throughout the enclosure. Such an immunization enclosure may be set up to accept a known quantity of a pathogenic source through air intake 202. An air mover 206 will move the pathogenic source from the air intake 202, through a UVC disinfection unit 208 which inactivates or neuters the virus without destroying the antigenic proteins. This treated air is then routed into the test chamber 210 where the treated air can be sampled to make sure that the pathogens are totally neutered before it is circulated throughout the immunization enclosure.

While the foregoing describes various embodiments of the invention, additional embodiments of the invention may be devised without departing from the basic scope thereof. The scope of the invention is determined by the claims that follow. The invention is not limited to the described embodiments, versions or examples, which are included to enable a person having ordinary skill in the art to make and use the invention when combined with information and knowledge available to the person having ordinary skill in the art.

I claim:

1. A system for delivering inactivated pathogens to an enclosure, comprising:

an air delivery system, the air delivery system comprising:

(a) an air intake;

(b) an air conditioning unit;

(c) an air mover;

(d) a UVC disinfection unit;

(e) an enclosure, wherein the enclosure is configured for holding animals or birds;

(f) an enclosure air entry vent;

(g) an enclosure air discharge vent;

(h) an air circulation pathway going from the air intake through an air duct connected at one end to the air intake and at a second end to the enclosure air entry vent that opens into the enclosure, wherein the air duct provides:

a passageway through the air delivery system; and a pathogen loading inlet connected to the air circulation pathway, wherein a predetermined quantity of pathogen is injected into the system.

2. The system as claimed in claim 1, wherein the air mover controls a velocity of air movement through the air duct.

3. The system as claimed in claim 1, wherein the UVC disinfection unit comprises a housing that encloses a disinfection chamber that has:

(a) a chamber wall;

(b) a chamber inlet;

(c) a chamber outlet;

(d) a centralized inner bore having an interior chamber surface facing the inner bore;

(e) a UVC light source positioned adjacent the interior chamber surface; and (f) a helical air flow diverter centralized within the inner bore proximal the UVC light source, wherein the helical airflow diverter creates a helical path for the air circulation pathway to proceed through the disinfection chamber from the chamber inlet to the chamber outlet.

4. The system as claimed in claim 3, wherein the air disinfection unit contains more than one UVC disinfection chamber.

5. The system as claimed in claim 1, wherein the enclosure is a free-standing, mobile enclosure.

* * * * *